(12) United States Patent
Ju

(10) Patent No.: US 8,889,348 B2
(45) Date of Patent: Nov. 18, 2014

(54) DNA SEQUENCING BY NANOPORE USING MODIFIED NUCLEOTIDES

(75) Inventor: Jingyue Ju, Englewood Cliffs, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 746 days.

(21) Appl. No.: 12/308,091

(22) PCT Filed: Jun. 7, 2007

(86) PCT No.: PCT/US2007/013559
§ 371 (c)(1),
(2), (4) Date: May 18, 2009

(87) PCT Pub. No.: WO2007/146158
PCT Pub. Date: Dec. 21, 2007

(65) Prior Publication Data
US 2009/0298072 A1    Dec. 3, 2009

Related U.S. Application Data

(60) Provisional application No. 60/811,912, filed on Jun. 7, 2006.

(51) Int. Cl.
*C12Q 1/68* (2006.01)
*C07H 21/04* (2006.01)

(52) U.S. Cl.
CPC .................................. *C12Q 1/6869* (2013.01)
USPC .......................................... 435/6.1; 536/23.1

(58) Field of Classification Search
None
See application file for complete search history.

(56) References Cited

U.S. PATENT DOCUMENTS

| | | | |
|---|---|---|---|
| 4,121,192 A | 10/1978 | Wilson | |
| 4,859,945 A | 8/1989 | Stokar | |
| 5,198,543 A | 3/1993 | Blanco et al. | |
| 5,302,509 A | 4/1994 | Cheeseman | |
| 5,308,539 A | 5/1994 | Koden et al. | |
| 5,457,342 A | 10/1995 | Herbst, II | |
| 5,569,950 A | 10/1996 | Lewis et al. | |
| 5,576,204 A | 11/1996 | Blanco et al. | |
| 5,756,355 A | 5/1998 | Lang et al. | |
| 5,770,367 A | 6/1998 | Southern et al. | |
| 5,795,782 A | 8/1998 | Church et al. | |
| 5,804,386 A | 9/1998 | Ju | |
| 5,814,454 A | 9/1998 | Ju | |
| 5,876,936 A | 3/1999 | Ju | |
| 5,912,155 A | 6/1999 | Chatterjee et al. | |
| 5,939,301 A | 8/1999 | Hughes, Jr. et al. | |
| 5,952,180 A | 9/1999 | Ju | |
| 6,012,291 A | 1/2000 | Ema | |
| 6,014,213 A | 1/2000 | Waterhouse et al. | |
| 6,015,714 A | 1/2000 | Baldarelli et al. | |
| 6,046,005 A | 4/2000 | Ju et al. | |
| 6,082,115 A | 7/2000 | Strnad | |
| 6,210,896 B1 | 4/2001 | Chan | |
| 6,217,731 B1 | 4/2001 | Kane et al. | |
| 6,232,103 B1 | 5/2001 | Short | |
| 6,255,083 B1 | 7/2001 | Williams | |
| 6,261,797 B1 | 7/2001 | Sorge et al. | |
| 6,265,193 B1 | 7/2001 | Brandis et al. | |
| 6,321,101 B1 | 11/2001 | Holmstrom | |
| 6,362,002 B1 * | 3/2002 | Denison et al. | 436/2 |
| 6,383,749 B2 * | 5/2002 | Bochkariov et al. | 435/6.11 |
| 6,399,320 B1 | 6/2002 | Markau et al. | |
| 6,399,335 B1 | 6/2002 | Kao et al. | |
| 6,413,792 B1 | 7/2002 | Sauer | |
| 6,485,703 B1 | 11/2002 | Cote et al. | |
| 6,607,883 B1 | 8/2003 | Frey et al. | |
| 6,616,895 B2 | 9/2003 | Dugas et al. | |
| 6,627,748 B1 | 9/2003 | Ju et al. | |
| 6,664,079 B2 | 12/2003 | Ju et al. | |
| 6,673,615 B2 | 1/2004 | Denison et al. | |
| 6,686,997 B1 | 2/2004 | Allen | |
| 6,723,513 B2 | 4/2004 | Lexow | |
| 6,746,594 B2 | 6/2004 | Akeson et al. | |
| 6,762,048 B2 | 7/2004 | Williams | |
| 6,794,177 B2 | 9/2004 | Markau et al. | |
| 6,800,933 B1 | 10/2004 | Mathews et al. | |
| 6,880,346 B1 | 4/2005 | Tseng et al. | |
| 6,891,278 B2 | 5/2005 | Muller et al. | |
| 6,916,665 B2 | 7/2005 | Bayley et al. | |
| 6,952,651 B2 | 10/2005 | Su | |
| 7,033,762 B2 | 4/2006 | Nelson et al. | |
| 7,041,812 B2 | 5/2006 | Kumar et al. | |
| 7,052,839 B2 | 5/2006 | Nelson et al. | |
| 7,057,026 B2 | 6/2006 | Barnes et al. | |
| 7,074,597 B2 | 7/2006 | Ju | |

(Continued)

FOREIGN PATENT DOCUMENTS

WO    WO 91/06678 A1    5/1991
WO    WO 93/21340 A1    10/1993

(Continued)

OTHER PUBLICATIONS

Pourmand N. et al. Nucleic Acids Research (2002) vol. 30, No. 7, pp. 1-5.* International Search Report issued by the International Searching Authority (ISA/US) on Oct. 29, 2007 in connection with International Application No. PCT/US2007/013559.
Written Opinion of the International Searching Authority issued by the International Searching Authority (ISA/US) on Oct. 29, 2007 in connection with International Application No. PCT/US2007/013559.
Ju J., et al. (1996) Cassette labeling for facile construction of energy transfer fluorescent primers. Nuc. Acids Res. 24 (6): 1144-1148.
J., et al. (1996) Energy transfer primers:, A new fluorescence labeling paradigm for DNA sequencing and analysis. Nature Medicine 2: 246-249.

(Continued)

*Primary Examiner* — Stephen Kapushoc
(74) *Attorney, Agent, or Firm* — John P. White; Cooper & Dunham LLP

(57) ABSTRACT

This invention provides a process for sequencing single-stranded DNA by employing a nanopore and modified nucleotides.

19 Claims, 10 Drawing Sheets

(56) References Cited

U.S. PATENT DOCUMENTS

| | | |
|---|---|---|
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,345,159 B2 | 3/2008 | Ju et al. |
| 7,368,668 B2 | 5/2008 | Ren et al. |
| 7,405,281 B2 | 7/2008 | Xu et al. |
| 7,446,017 B2 | 11/2008 | Liu et al. |
| 7,452,698 B2 | 11/2008 | Sood et al. |
| 7,622,279 B2 | 11/2009 | Ju |
| 7,622,934 B2 | 11/2009 | Hibbs et al. |
| 7,625,701 B2 | 12/2009 | Williams et al. |
| 7,635,578 B2 | 12/2009 | Ju et al. |
| 7,710,479 B2 | 5/2010 | Nitta et al. |
| 7,713,698 B2 | 5/2010 | Ju et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,790,869 B2 | 9/2010 | Ju et al. |
| 7,871,777 B2 | 1/2011 | Schneider et al. |
| 7,883,869 B2 | 2/2011 | Ju et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,982,029 B2 | 7/2011 | Ju et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,058,414 B2 | 11/2011 | Menchen et al. |
| 8,088,575 B2 | 1/2012 | Ju et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,192,961 B2 | 6/2012 | Williams |
| 8,252,911 B2 | 8/2012 | Bjornson et al. |
| 8,257,954 B2 | 9/2012 | Clark et al. |
| 8,298,792 B2 | 10/2012 | Ju et al. |
| 2003/0027140 A1 | 2/2003 | Ju et al. |
| 2003/0054360 A1 | 3/2003 | Gold et al. |
| 2003/0101006 A1 | 5/2003 | Mansky et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0185466 A1 | 9/2004 | Ju et al. |
| 2005/0032081 A1 | 2/2005 | Ju et al. |
| 2005/0091989 A1 | 5/2005 | Leija et al. |
| 2005/0186576 A1 | 8/2005 | Chan et al. |
| 2005/0208574 A1 | 9/2005 | Bayley et al. |
| 2005/0221351 A1 | 10/2005 | Ryu |
| 2005/0239134 A1 | 10/2005 | Gorenstein et al. |
| 2006/0057565 A1 | 3/2006 | Ju et al. |
| 2006/0105461 A1 | 5/2006 | Tom-Moy et al. |
| 2006/0115951 A1 | 6/2006 | Mosley |
| 2006/0252038 A1 | 11/2006 | Ju |
| 2007/0173731 A1 | 7/2007 | Meka et al. |
| 2007/0190542 A1 | 8/2007 | Ling et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0199932 A1 | 8/2008 | Hanzel et al. |
| 2008/0218184 A1 | 9/2008 | White et al. |
| 2008/0286768 A1 | 11/2008 | Lexow |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 | 5/2009 | Gershow et al. |
| 2009/0167288 A1 | 7/2009 | Reid et al. |
| 2009/0215050 A1 | 8/2009 | Jenson |
| 2009/0263791 A1 | 10/2009 | Ju et al. |
| 2009/0325154 A1 | 12/2009 | Ju |
| 2010/0025238 A1 | 2/2010 | Gottlieb et al. |
| 2010/0025249 A1 | 2/2010 | Polonsky et al. |
| 2010/0035260 A1 | 2/2010 | Olasagasti et al. |
| 2010/0047802 A1 | 2/2010 | Bjornson et al. |
| 2010/0072080 A1 | 3/2010 | Karhanek et al. |
| 2010/0075328 A1 | 3/2010 | Bjornson et al. |
| 2010/0075332 A1 | 3/2010 | Patel et al. |
| 2010/0078777 A1 | 4/2010 | Barth et al. |
| 2010/0093555 A1 | 4/2010 | Bjornson et al. |
| 2010/0148126 A1 | 6/2010 | Guan et al. |
| 2010/0243449 A1 | 9/2010 | Oliver |
| 2010/0261247 A1 | 10/2010 | Hanzel et al. |
| 2010/0297644 A1 | 11/2010 | Kokoris et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014611 A1 | 1/2011 | Ju et al. |
| 2011/0039259 A1 | 2/2011 | Ju et al. |
| 2011/0059505 A1 | 3/2011 | Hanzel et al. |
| 2011/0160093 A1 | 6/2011 | Van den Boom et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0142006 A1 | 6/2012 | Ju et al. |
| 2012/0156680 A1 | 6/2012 | Ju et al. |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2013/0264207 A1 | 10/2013 | Ju et al. |
| 2013/0280700 A1 | 10/2013 | Ju et al. |
| 2014/0093869 A1 | 4/2014 | Ju et al. |

FOREIGN PATENT DOCUMENTS

| | | |
|---|---|---|
| WO | WO 97/32999 A1 | 9/1997 |
| WO | WO 97/46704 A1 | 12/1997 |
| WO | WO 01/48235 A2 | 7/2001 |
| WO | WO 02/22883 | 3/2002 |
| WO | WO 02/29003 | 4/2002 |
| WO | WO 02/29003 A3 | 7/2002 |
| WO | WO 02/079519 | 10/2002 |
| WO | WO 03/020734 A2 | 3/2003 |
| WO | WO 2004/007773 | 1/2004 |
| WO | WO 2004/055160 | 1/2004 |
| WO | WO 2004/055160 A3 | 8/2004 |
| WO | WO 2004/071155 A2 | 8/2004 |
| WO | WO 2004/072238 A2 | 8/2004 |
| WO | WO 2005/084367 | 9/2005 |
| WO | WO 2005/084367 A3 | 12/2005 |
| WO | WO 2007/002204 | 1/2007 |
| WO | WO 2007/053702 | 5/2007 |
| WO | WO 2007/053719 | 5/2007 |

(56) References Cited

FOREIGN PATENT DOCUMENTS

| WO | WO 2007/062105 | 5/2007 |
|---|---|---|
| WO | WO 2007/127327 A2 | 11/2007 |
| WO | WO 2007/146158 A1 | 12/2007 |
| WO | WO 2007/053702 A3 | 1/2008 |
| WO | WO 2008/034602 A2 | 3/2008 |
| WO | WO 2008/069973 | 6/2008 |
| WO | WO 2008/102120 A1 | 8/2008 |
| WO | WO 2008/129107 A1 | 10/2008 |
| WO | WO 2008/034602 A3 | 2/2009 |
| WO | WO 2009/020682 A2 | 2/2009 |
| WO | WO 2007/002204 A3 | 4/2009 |
| WO | WO 2007/053719 A3 | 4/2009 |
| WO | WO 2007/062105 A3 | 4/2009 |
| WO | WO 2008/069973 A3 | 6/2009 |
| WO | WO 2010/109197 A2 | 9/2010 |
| WO | WO 2011/038241 A1 | 3/2011 |
| WO | WO 2011/097028 A1 | 8/2011 |
| WO | WO 2011/106459 A2 | 9/2011 |
| WO | WO 2012/009578 A2 | 1/2012 |
| WO | WO 2012/121756 A1 | 9/2012 |
| WO | WO 2013/154999 A2 | 10/2013 |
| WO | WO 2013/191793 A1 | 12/2013 |

OTHER PUBLICATIONS

Ju J., et al. (1995) Fluorescence energy transfer dye labeled primers for DNA sequencing and analysis. Proc. Natl. Acad. Sci. USA 92: 4347-4351.

Ju J., et al. (2006) Four color DNA sequencing by synthesis using cleavable fluorescent nucleotide reversible terminators. Proc Natl Acad Sci USA 103: 19635 40.

Notification Concerning Transmittal of International Preliminary Report on Patentability issued Dec. 24, 2008 in connection with International Application No. PCT/US07/13559.

Akeson, M., Branton, D., Kasianowicz, J.J., Brandin, E. and Deamer, D.W. Microsecond time- scale discrimination between polycytidylic acid and polyadenylic acid segments within single RNA molecules. Biophys. J. 1999, 77, 3227-3233.

Bai, X., Kim, S., Li, Z., Turro, N.J. and Ju, J. Design and synthesis of a photocleavable biotinylated nucleotide for DNA analysis by mass spectrometry. Nucleic Acids Research 2004, 32(2).

Bezrukov, S.M., and Kasianowicz, J.J. Neutral polymers in the nanopores of alamethicin and alpha-hemolysin. Biologicheskie Membrany 2001, 18, 451-455.

Chandler, E.L. , Smith, A.L., Burden, L.M., Kasianowicz and Burden, D. L. Membrane Surface Dynamics of DNA-Threaded Nanopores Revealed by Simultaneous Single-Molecule Optical and Ensemble Electrical Recording. Langmuir 2004, 20, 898-905.

Deamer, D.W. and Branton, D. Characterization of nucleic acids by nanopore analysis. Acc. Chem. Res. 2002, 35(10), 817-825.

S.E., Sidorov A., Gourlain T., Mignet N., Thorpe S.J., Brazier J.A. , Dickman M.J. , Hornby D. P., Grasby, J.A. and Williams, D.M. Enhancing the catalytic repertoire of nucleic acids: a systematic study of linker length and rigidity. Nucleic Acids Research 2001, 29(7), 1565-1573.

Henrickson, S. E., Misakian, M., Robertson, B. and Kasianowicz, J.J. Driven asymmetric DNA transport in a nanometer-scale pore. Physical Review Letters 2000, 85, 3057-3060.

Kasianowicz, J.J., Brandin, B., Branton, D. and Deamer, D.W. Characterization of individual polynucleotide molecules using a membrane channel. Proc. Natl. Acad. Sci. USA 1996, 93, 13770-13773.

Kasianowicz, J.J. Nanometer-scale pores: potential applications for DNA characterization and analyte detection. Disease Markers 2003, 18, 185-191.

Kasianowicz,. J.J. Nanopore. Flossing with DNA. Nature Materials 2004, 3, 355-356.

Lundquist, J. T. and Pelletier, J. C. A New Tri- Orthogonal Strategy for Peptide Cyclization. Org. Lett. 2002, 4(19), 3219-3221.

L., Stein, D., McMullan, C, Branton, D., Aziz, M.J. and Golovchenko, J.A. Ion-beam sculpting at nanometre length scales. Nature 2001, 412, 166-169.

Z., Bai, X., Ruparel, H., Kim, S., Turro, N.J. and Ju, J. A photocleavable fluorescent nucleotide for DNA sequencing and analysis. Proc. Natl. Acad. Sci. USA 2003, 100, 414-419.

Meller, A., Nivon, L., Brandin, E., Golovchenko, J. and Branton, D. Rapid nanopore discrimination between single polynucleotide molecules. Proc. Natl. Acad. Sci. USA 2000, 97, 1079-1084.

Perkins, T.T., Quake, S.R., Smith, D. E. and Chu, S. Relaxation of a single DNA molecule observed by optical microscopy. Science 1994, 264, 822-826.

Rief, M., Clausen-Schaumann, H. and Gaub, H. E. Sequence-dependent mechanics of single DNA molecules. Mat. Struct. Biol. 1999, 6, 346-349.

Rosenblum, B.B., Lee, L. G., Spurgeon, S. L., Khan, S.H., Menchen, S.M., Heiner, CR. and Chen, S.M. New dye-labeled terminators for improved DNA sequencing patterns. Nucleic Acids Research 1997, 25(22), 4500-4504.

Rostovtsev, V.V., Green, L.G. , Fokin, V.V. and Sharpless, K. B. A stepwise huisgen cycloaddition process: copper(I)-catalyzed regioselective "ligation" of azides and terminal alkynes. Angew. Chem. Int. Ed. 2002, 41(14), 2596-2599.

Seo, T. S., Bai, X., Ruparel, H., Li, Z., Turro, N.J. and Ju, J. Photocleavable fluorescent nucleotides for DNA sequencing on a chip constructed by site-specific coupling chemistry. Proc. Natl. Acad. Sci. USA 2004, 101, 5488-5493.

Singh, S. B. and Tomassini, J. E. Synthesis of natural flutimide and analogous fully substituted pyrazine-2,6-diones, endonuclease inhibitors of influenza virus. J. Org. Chem. 2001, 66(16), 5504-5516.

Smith, S.B., Cui, Y. and Bustamante, C. Overstretching B-DNA: the elastic response of individual double-stranded and single-stranded DNA molecules. Science 1996, 271, 795-799.

Streater, M., Taylor, P. D., Hider, R. C, and Porter, J. Novel 3-hydroxy-2 (IH) -pyridinones. Synthesis, iron (III)—chelating properties, and biological activity. J. Medicinal Chem. 1990, 33(6), 1749-1755.

Vercoutere, W., Winters-Hilt, S., Olsen, H., Deamer, D., Haussler, D. and Akeson, M. Rapid discrimination among individual DNA hairpin molecules at single-nucleotide resolution using an ion channel. Nat. Biotech 2001, 19, 248-252.

Heng, J. B. et al., The Electromechanics of DNA in a synthetic Nanopore. Biophysical Journal 2006, 90, 1098-1106.

Fologea, D. et al., Detecting Single Stranded DNA with a Solid State Nanopore. Nano Letters 2005 5(10), 1905-1909.

Heng, J. B. et al., Stretching DNA Using the Electric Field in a Synthetic Nanopore. Nano Letters 2005 5(10), 1883-1888.

Fologea, D. et al., Slowing DNA Translocation in a Solid State Nanopore. Nano Letters 2005 5(9), 1734-1737.

Bokhari, S. H. and Sauer, J. R., A Parallel Graph Decomposition Algorithm for DNA Sequencing with Nanopores. Bioinformatics 2005 21(7), 889-896.

Mathe, J. et al., Nanopore Unzipping of Individual Hairpin Molecules. Biophysical Journal 2004 87, 3205-3212.

Aksimentiev, A. et al., Microscopic Kinetics of DNA Translocation through Synthetic Nanopores. Biophysical Journal 2004 87, 2086-2097.

Wang, H. et al., DNA heterogeneity and Phosphorylation unveiled by Single-Molecule Electrophoresis. Proc. Natl. Acad. Sci. USA 2004 101(37), 13472-13477.

Sauer-Budge, A. F. et al., Unzipping Kinetics of Double Stranded DNA in a Nanopore. Physical Review Letters 2003 90(23), 238101-1-238101-4.

Vercoutere, W.A. et al., Discrimination Among Individual Watson-Crick Base Pairs at the Terminin of Single DNA Hairpin Molecules. Nucleic Acids Research 2003 31(4), 1311-1318.

Meller, A. et al., Single Molecule Measurements of DNA Transport Through a Nanopore. Electrophoresis 2002 23, 2583-2591.

Oct. 12, 2013 Decision of Rejection issued in connection with Chinese Patent Application No. 200780028545.1 (with English translation).

U.S. Appl. No. 13/959,660, filed Aug. 5, 2013, Ju et al.
U.S. Appl. No. 14/119,846, filed Nov. 22, 2013, Ju et al.
U.S. Appl. No. 14/242,487, filed Apr. 1, 2014, Ju et al.
Pending claims in U.S. Appl. No. 11/922,385, filed Dec. 14, 2007, Ju et al.

(56) References Cited

OTHER PUBLICATIONS

Allowed claims in U.S. Appl. No. 12/084,457, filed Apr. 30, 2008, Ju et al.
Pending claims in U.S. Appl. No. 13/186,353, filed Jul. 19, 2011, Ju et al.
Pending claims in U.S. Appl. No. 13/959,660, filed Aug. 5, 2013, Ju et al.
Jun. 22, 2011 Office Action in connection with Chinese Patent Application No. 200780028545.1 (with English translation of cover page only).
Jul. 2, 2012 Second Office Action in connection with Chinese Patent Application No. 200780028545.1.
Apr. 9, 2013 Third Office Action in connection with Chinese Patent Application No. 200780028545.1.
International Search Report and Written Opinion of the International Searching Authority mailed Feb. 4, 2013 in connection with PCT International Application No. PCT/US2011/065640.
International Search Report and Written Opinion of the International Searching Authority mailed Oct. 25, 2013 in connection with PCT International Application No. PCT/US2013/035635.
Robertson et al., "Single-Molecule Mass Spectrometry in Solution Using a Solitary Nanopore" PNAS, 104(20):8207-8211.
Invitation to Pay Additional Fees mailed by the International Searching Authority on Aug. 19, 2013 connection with PCT International Application No. PCT/US2013/035635.
International Search Report and Written Opinion of the International Searching Authority mailed Sep. 24, 2013 in connection with PCT International Application No. PCT/US2013/035630.
Apr. 16, 2014 Communication transmitting Supplementary European Search Report and European Search Opinion in connection with European Patent Application No. EP 11848220.
Eid et al., "Real-Time DNA Sequencing from Single Polymerase Molecules", Science, 23(5910):133-138 (2008).
Guranowski et al., "Selective Degradation of 2'-Adenlyated Diadenosine Tri- and Tetraphosphates, $Ap_3A$ and $Ap_4A$, by Two Specific Human Dinucleoside Polyphosphate Hydrolases", Archives of Biochemistry and Biophysics, 373(1):218-224 (2000).
Ju et al., "Four-color DNA Sequencing by Synthesis using Cleavable Fluorescent Nucleotide Reversible Terminators", PNAS, 103(52):19635-19640 (2006).
Kumar et al., "Terminal phosphate labeled nucleotides: Synthesis, applications, and linker effect on incorporation by DNA polymerases", Nucleosides, Nucleotides, and Nucleic Acids, 24(5-7):401-108 (2005).
Mulder et al., "Nucleotide modification at the γ-phosphate leads to the improved fidelity of HIV-1 reverse transcriptase", Nucleic Acids Research, 33(15):4865-4873 (2005).
Reynolds et al., "Synthesis and Stability of Novel Terminal Phosphate-labeled Nucleotides", Nucleosides, Nucleotides, and Nucleic Acids, 27(1):18-30 (2008).
Sood et al., "Terminal phosphate-labeled nucleotides with improved substrate properties for homogenous nucleic acid assays", JACS, 127(8):2394-2395 (2005).
Mar. 27, 2014 Office Action in connection with Chinese Patent Application No. 201180063978.7 (with English translation of cover page only).
U.S. Appl. No. 13/396,522, filed Feb. 14, 2012, Chen.
Andersen. Sequencing and the single channel. Biophys J. Dec. 1999; 77(6):2899-901.
Ashkenasy, et al. Recognizing a single base in an individual DNA strand: a step toward DNA sequencing in nanopores. Angew Chem Int Ed Engl. Feb. 18, 2005; 44(9):1401-4.
Atanasov, et al. Membrane on a chip: a functional tethered lipid bilayer membrane on silicon oxide surfaces. Biophys J. Sep. 2005; 89(3):1780-8.
Baaken, et al. Planar microelectrode-cavity array for high-resolution and parallel electrical recording of membrane ionic currents. Lab Chip. Jun. 2008; 8(6):938-44. Epub Apr. 16, 2008.
Benner, et al. Sequence-specific detection of individual DNA polymerase complexes in real time using a nanopore. Nat Nanotechnol. Nov. 2007; 2(11):718-24. Epub Oct. 28, 2007.
Boireau, et al. Unique supramolecular assembly of a redox protein with nucleic acids onto hybrid bilayer: towards a dynamic DNA chip. Biosens Bioelectron. Feb. 15, 2005; 20(8):1631-7.
Buchmann, et al. Electrochemical release from gold-thiolate electrodes for controlled insertion of ion channels into bilayer membranes. Bioorg Med Chem. Mar. 15, 2004; 12(6):1315-24.
Butler, et al. Ionic current blockades from DNA and RNA molecules in the alpha-hemolysin nanopore. Biophys J. Nov. 1, 2007; 93(9):3229-40. Epub Aug. 3, 2007.
Butler, et al. Determination of RNA orientation during translocation through a biological nanopore. Biophys J. Jan. 1, 2006; 90(1):190-9. Epub Oct. 7, 2005.
Butler, et al. Single-molecule DNA detection with an engineered MspA protein nanopore. Proc Natl Acad Sci. U S A. Dec. 30, 2008; 105(52):20647-52. Epub Dec. 19, 2008.
Clarke, et al. Continuous base identification for single-molecule nanopore DNA sequencing. Nat Nanotechnol. Apr. 2009; 4(4):265-70. Epub Feb. 22, 2009.
Cockroet, et al. A single-molecule nanopore device detects DNA polymerase activity with single-nucleotide resolution. J Am Chem Soc. Jan. 23, 2008; 130(3):818-20. Epub Jan. 1, 2008.
Danelon, et al. Cell membranes suspended across nanoaperture arrays. Langmuir. Jan. 3, 2006; 22(1):22-5.
Derrington, et al. Nariopore DNA sequencing with MspA. Proc Natl Aced Sci U S A. Sep. 14, 2010; 107(37):16060-5. Epub Aug. 26, 2010.
Ervin, et al. Simultaneous alternating and direct current readout of protein ion channel blocking events using glass nanopore membranes. Anal Chem. Mar. 15, 2008; 80(6):2069-76. Epub Feb. 23, 2008.
Flusberg, et al. Direct detection of DNA methylation during single-molecule, real-time sequencing. Nat Methods. Jun. 2010; 7(6):461-5. Epub May 9, 2010.
Harlepp, et al. Probing complex RNA structures by mechanical force. Eur Phys J E Soft Matter. Dec. 2003; 12(4):605-15.
Holden, et al. Direct introduction of single protein channels and pores into lipid bilayers. J Am Chem Soc. May 11, 2005; 127(18):6502-3.
Holden, et al. Direct transfer of membrane proteins from bacteria to planar bilayers for rapid screening by single-channel recording. Nat Chem Biol. Jun. 2006; 2(6):314-8. Epub May 7, 2006.
Hromada, et al. Single molecule measurements within individual membrane-bound ion channels using a polymer-based bilayer lipid membrane chip. Lab Chip. Apr. 2008; 8(4):602-8. Epub Feb. 29, 2008.
International Search Report and Written Opinion issued May 3, 2012 in connection with PCT/US2012/020827.
International Search Report and Written Opinion issued Jul. 8, 2011 in connection with PCT/US2011/064490.
International Search Report and Written Opinion issued Aug. 28, 2012 in connection with PCT/US2011/066627.
International Search Report and Written Opinion issued Aug. 28, 2012 in connection with PCT/US2011/066632.
International Search Report and Written Opinion issued Nov. 5, 2012 in connection with PCT/US2011/064490.
Jurak, et al. Wettability and topography of phospholipid DPPC multilayers deposited by spin-coating on glass, silicon, and mica slides. Langmuir. Sep. 25, 2007; 23(20):10156-63. Epub Aug. 28, 2007.
Kang, et al. A storable encapsulated bilayer chip containing a single protein nanopore. J Am Chem Soc. Apr. 18, 2007; 129(15):4701-5. Epub Mar. 22, 2007.
Kawano, et al. Controlling the translocation of single-stranded DNA through alpha-hemolysin ion channels using viscosity. Langmuir. Jan. 20, 2009; 25(2):1233-7.
Kumar, et al. PEG-labeled nucleotides and nanopore detection for single molecule DNA sequencing by synthesis. Sci Rep. 2012; 2:684. Epub Sep. 21, 2012.
Kutik, et al. Dissecting membrane insertion of mitochondrial beta-barrel proteins. Cell. Mar. 21, 2008; 132(6):1011-24.

(56) References Cited

OTHER PUBLICATIONS

Linear Technology, High Efficiency Thermoelectric Cooler Controller, 2001.
Low Noise, Dual Switched Integrator, Burr-Brown Corporation, Sep. 1994.
Madampage, et al. Nanopore detection of antibody prion interactions. Anal Biochem. Jan. 1, 2010; 396(1):36-41. Epub Aug. 21, 2009.
Maurer, et al. Reconstitution of ion channels in agarose-supported silicon orifices. Biosens Bioelectron. May 15, 2007; 22(11):2577-84. Epub Nov. 13, 2006.
McNally, et al. Optical recognition of converted DNA nucleotides for single-molecule DNA sequencing using nanopore arrays. Nano Lett. Jun. 9, 2010; 10(6):2237-44.
Mohammad, et al. Controlling a single protein in a nanopore through electrostatic traps. J Am Chem Soc. Mar. 26, 2008; 130(12):4081-3. Epub Mar. 6, 2008.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Office Action issued Apr. 26, 2012 in connection with U.S. Appl. No. 12/658,591.
Office Action issued Apr. 26, 2012 in connection with U.S. Appl. No. 12/658,601.
Office Action issued Jun. 15, 2012 in connection with U.S. Appl. No. 12/658,604.
Office Action issued Aug. 3, 2012 in connection with U.S. Appl. No. 12/658,602.
Office Action issued Oct. 2, 2012 in connection with U.S. Appl. No. 12/658,603.
Office Action issued Oct. 16, 2012 in connection with U.S. Appl. No. 12/658,601.
Office Action issued Oct. 25, 2012 in connection with U.S. Appl. No. 12/658,591.
Oxford Nanopore Technologies, Sensor Array Chip, Jul. 14, 2011.
Park, et al. DNA hybridization sensors based on electrochemical impedance spectroscopy as a detection tool. Sensors (Basel). 2009; 9(12):9513-32. Epub Nov. 26, 2009.
Purnell, et al. Discrimination of single base substitutions in a DNA strand immobilized in a biological nanopore. ACS Nano. Sep. 22, 2009; 3(9):2533-8.
Rotem et al., Temperature Measurement in the Intel Core Duo Processor, 2007.
Sanchez-Magraner, et al. Membrane insertion of *Escherichia coli* alpha-hemolysin is independent from membrane lysis. J Biol Chem. Mar. 3, 2006; 281(9):5461-7. Epub Dec. 22, 2005.
Shim, et al. Encapsulating a single G-quadruplex aptamer in a protein nanocavity. J Phys Chem B. Jul. 17, 2008; 112(28):8354-60. Epub Jun. 19, 2008.
Simon, et al. Formation and stability of a suspended biomimetic lipid bilayer on silicon submicrometer-sized pores. J Colloid Interface Sci. Apr. 15, 2007; 308(2):337-43. Apub Jan. 31, 2007.
Singer et al., Nanopore Based Sequence Specific Detection of Duplex DNA for Genomic Profiling, Jan. 8, 2010, published Jan. 20, 2010, pp. 738-742.
Stefureac, et al. Nanopore analysis of the interaction of metal ions with prion proteins and peptides. Biochem Cell Biol. Apr. 2010; 88(2):347-58.
Stefureac, et al. Transport of alpha-helical peptides through alpha-hemolysin and aerolysin pores. Biochemistry. Aug. 1, 2006; 45(30):9172-9.
Stoddart, et al. Nucleobase recognition in ssDNA at the central constriction of the alpha-hemolysin pore. Nano Lett. Sep. 8, 2010; 10(9):3633-7.
Studer, et al. Formation of individual protein channels in lipid bilayers suspended in nanopores. Colloids Surf B Biointerfaces. Oct. 15, 2009; 73(2):325-31. Epub Jun. 10, 2009.
Suzuki, et al. Highly reproducible method of planar lipid bilayer reconstitution in polymethyl methacrylate microfluidic chip. Langmuir. Feb. 14, 2006; 22(4):1937-42.
Thomson et al. Preliminary nanopore cheminformatics analysis of aptamer-target binding strength. BMC Bioinformatics. Nov. 1, 2007; 8 Suppl 7:S11.
Viasnoff, et al. Probing DNA base pairing energy profiles using a nanopore. Eur Biophys J. Feb. 2009; 38(2):263-9. Epub Oct. 3, 2008.
Wanunu, et al. DNA profiling using solid-state nanopores: detection of DNA-binding molecules. Nano Lett. Oct. 2009; 9(10):3498-502.
Weng, et al. Fluid biomembranes supported on nanoporous aerogel/xerogel substrates. Langmuir. Aug. 17, 2004; 20(17):7232-9.
Wilson, et al. Electronic control of DNA polymerase binding and unbinding to single DNA molecules. ACS Nano. Apr. 28, 2009; 3(4):995-1003.
Wilson, et al. Feedback control of a DNA molecule tethered in a nanopore to repeatedly probe DNA-binding enzymes. Conf Proc IEEE Eng Med Biol Soc. 2008; 2008:5745-8.
Winters-Hilt, et al. Nanopore-based kinetics analysis of individual antibody-channel and antibody-antigen interactions. BMC Bioinformatics. Nov. 1, 2007; 8 Suppl 7:S20.
Woodside, et al. Direct measurement of the full, sequence-dependent folding landscape of a nucleic acid. Science. Nov. 10, 2006; 314(5801):1001-4.
Woodside, et al. Nanomechanical measurements of the sequence-dependent folding landscapes of single nucleic acid hairpins. Proc Nati Acad Sci U S A. Apr. 18, 2006; 103(16):6190-5. Epub Apr. 10, 2006.
Wu, et al. Single-molecule detection of nitrogen mustards by covalent reaction within a protein nanopore. J Am Chem Soc. May 28, 2008; 130(21):6813-9. Epub Apr. 30, 2008.
Zeineldin, et al. Using bicellar mixtures to form supported and suspended lipid bilayers on silicon chips. Langmuir. Sep. 12, 2006; 22(19):8163-8.
Zwolak, et al. Electronic signature of DNA nucleotides via transverse transport. Nano Lett. Mar. 2005; 5(3):421-4.
Jun. 22, 2011 First Office Action issued in connection with Chinese Patent Application No. 200780028545.1.
Jul. 2, 2012 Second Office Action issued in connection with Chinese Patent Application No. 200780028545.1.
U.S. Appl. No. 13/918,626, filed Jun. 14, 2013, Davis et al.
International Search Report issued Mar. 18, 2013 in connection with PCT Application No. PCT/U82012/063099.
International Search Report issued May 9, 2013 in connection with PCT Application No. PCT/US2013/028058.
International Search Report issued May 16, 2013 in connection with PCT Application No. PCT/US2013/026514.
International Search Report issued May 16, 2013 in connection with PCT Application No. PCT/US2013/022273.
Office Action issued Feb. 25, 2013 in connection with U.S. Appl. No. 13/396,522.
Sioddart, et al. Single-nucleotide discriminationin immobilized DNA oligonucleotides with a biological nanopore. Proc Natl Acad Sci U S A. May 12, 2009;106(19):7702-7. doi: 10.1073/pnas.0901051106. Epub Apr. 20, 2009.
UK search and examination report dated Feb. 25, 2013 for GB Application No. 1216656.7.
UK search and examination report dated May 1, 2013 for GB pplication No. 1216026.3.
Jan. 6, 2012 Response to First Office Action filed in connection with Chinese Patent Application No. 200780028545.1.
Nov. 19, 2012 Response to Second Office Action filed in connection with Chinese Patent Application No. 200780028545.1.
Jun. 21, 2013 Response to Third Office Action filed in connection with Chinese Patent Application No. 200780028545.1.
Jan. 26, 2014 Request for Reexamination filed in connection with Chinese Patent Application No. 200780028545.1.

* cited by examiner

SEQUENCE LISTING

<160> NUMBER OF SEQ ID NOS: 9

<210> SEQ ID NO 1
<211> LENGTH: 10
<212> TYPE: DNA

```
<213> ORGANISM: Artificial Sequence
<220> FEATURE:
<223> OTHER INFORMATION: Chemically Synthesized Sequence

<400> SEQUENCE: 1
tcgagctgca                                                            10

<210> SEQ ID NO 2
<211> LENGTH: 10
<212> TYPE: RNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 2
ugcagcucga                                                            10

<210> SEQ ID NO 3
<211> LENGTH: 50
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 3
aaaaaaaaaa aaaaaaaaaa aaaaaaaaaa aaaaaaaaaa aaaaaaaaaa                50

<210> SEQ ID NO 4
<211> LENGTH: 50
<212> TYPE: DNA
<213> ORGANISM: ARTIFICIAL SEQUNCE
<220> FEATURE:
<223> OTHER INFORMATION: CHEMICALLY SYNTHESIZED SEQUENCE

<400> SEQUENCE: 4
cccccccccc cccccccccc cccccccccc cccccccccc cccccccccc                50

<210> SEQ ID NO 5
<211> LENGTH: 50
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 5
gggggggggg gggggggggg gggggggggg gggggggggg gggggggggg                50

<210> SEQ ID NO 6
<211> LENGTH: 50
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 6
tttttttttt tttttttttt tttttttttt tttttttttt tttttttttt                50

<210> SEQ ID NO 7
<211> LENGTH: 60
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 7
aaaaaaaaaa aaaaaaaaaa aaaaaaaaaa tttttttttt tttttttttt tttttttttt     60
```

```
<210> SEQ ID NO 8
<211> LENGTH: 40
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 8
aaaaaaaaaa cccccccccc gggggggggg tttttttttt                          40

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 9
aaacccgggt ttcccgggaa attt                                           24
```

DNA SEQUENCING BY NANOPORE USING MODIFIED NUCLEOTIDES

This application is a §371 national stage of PCT International Application No. PCT/US2007/013559, filed Jun. 7, 2007, and claims the benefit of U.S. Provisional Application No. 60/811,912, filed Jun. 7, 2006, the contents of all of which are hereby incorporated by reference into this application.

The invention disclosed herein was made with government support under grant no. 1R21HG003718-01 from the National Human Genome Research Institute. Accordingly, the U.S. Government has certain rights in this invention.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

DNA sequencing is a fundamental technology for biology. Several analytical methods have been developed to detect DNA or RNA at the single molecule level using chemical or physical microscopic technologies [15, 16, 21 and 23]. In the past few years, the ion channel has been explored for detecting individual DNA or RNA strands, with nanopore being a candidate for high rate sequencing and analysis of DNA [9, 10, 4, 3 and 7].

In 1996, Kasianowicz et al. first demonstrated that the α-hemolysin channel, an exotoxin secreted by a bacterium, could be used to detect nucleic acids at the single molecule level [8]. The monomeric polypeptide self-assembles in a lipid bilayer membrane to form a heptameric pore, with a 2.6 nm-diameter vestibule and 1.5 nm-diameter limiting aperture (namely, the narrowest point of the pore) [1, 14 and 15]. In an aqueous ionic salt solution such as KCl, the pore formed by the α-hemolysin channel conducts a sufficiently strong and steady ionic current when an appropriate voltage is applied across the membrane. The limiting aperture of the nanopore allows linear single-stranded but not double-stranded nucleic acid molecules (diameter ~2.0 nm) to pass through. The polyanionic nucleic acids are driven through the pore by the applied electric field, which blocks or reduces the ionic current that would be otherwise unimpeded. This process of passage generates an electronic signature (FIG. 1) [23 and 5]. A particular nucleic acid molecule, when entering and passing through the nanopore, will generate a characteristic signature that distinguishes it from others. The duration of the blockade is proportional to the length of the nucleic acid, and its signal strength is related to the steric and electronic properties of the nucleotides, namely the identity of the four bases (A, C, G and T).

A specific event diagram is constructed which is the plot of translocation time versus blockade current. This specific event diagram (also referred to as an electronic signature) is used to distinguish the lengths and the compositions of polynucleotides by single-channel recording techniques based on characteristic parameters such as translocation current, translocation duration, and their corresponding dispersions in the diagram [14].

Although the nanopore approach is known as a DNA detection method, this approach for base-to-base sequencing has not yet been achieved.

SUMMARY OF THE INVENTION

This invention provides a method for determining the nucleotide sequence of a single-stranded DNA comprising the steps of:
(a) passing the single-stranded DNA through a pore of suitable diameter by applying an electric field to the DNA, wherein at least each A or each G residue and at least each C, each T or each U residue comprises a modifying group bound to its respective base so that each type of nucleotide in the DNA has an electronic signature which is distinguishable from the electronic signature of each other type of nucleotide in the DNA;
(b) for each nucleotide of the DNA which passes through the pore, determining an electronic signature for such nucleotide; and
(c) comparing each electronic signature determined in step (b) with electronic signatures corresponding to each of A, G, C and T modified as per the nucleotides in the single-stranded DNA, so as to determine the identity of each such nucleotide, thereby determining the nucleotide sequence of the single-stranded DNA.

This invention also provides a method for determining the nucleotide sequence of a single-stranded RNA comprising the steps of:
(a) passing the single-stranded RNA through a pore of suitable diameter by applying an electric field to the RNA, wherein at least each A or each G residue and at least each C or each U residue comprises a modifying group bound to its respective base so that each type of nucleotide in the RNA has an electronic signature which is distinguishable from the electronic signature of each other type of nucleotide in the RNA;
(b) for each nucleotide of the RNA which passes through the pore, determining an electronic signature for such nucleotide; and
(c) comparing each electronic signature determined in step (b) with electronic signatures corresponding to each of A, G, C and U modified as per the nucleotides in the single-stranded RNA, so as to determine the identity of each such nucleotide, thereby determining the nucleotide sequence of the single-stranded RNA.

This invention also provides a nucleotide having an azido group covalently bound to its base.

This invention also provides a method for making a modified nucleotide comprising contacting the instant nucleotide with an alkyne-containing compound under conditions permitting reaction between the azido and the alkyne groups, thereby making the modified nucleotide.

DETAILED DESCRIPTION OF THE INVENTION

Terms

Figure 1:
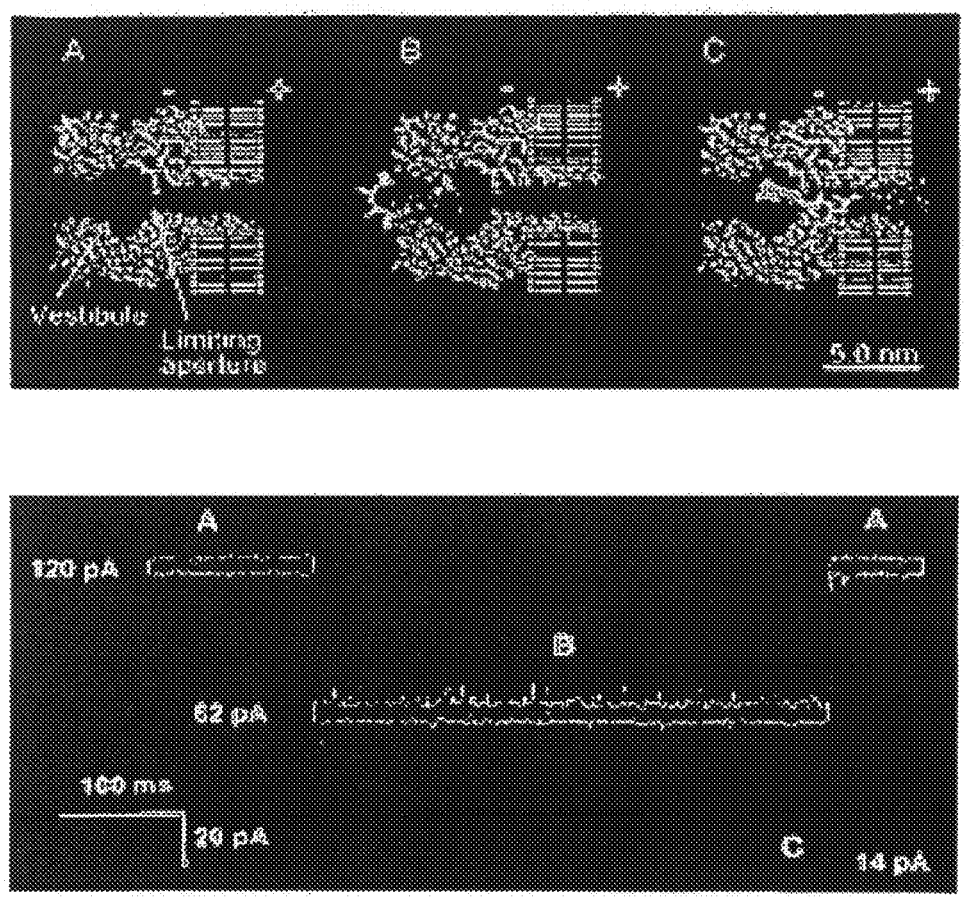
FIG. 1. α-Hemolysin protein self-assembles in a lipid bilayer to form an ion channel and a nucleic acid stretch passes through it (left), with the corresponding electronic signatures, generated (right) [23 and 5].

As used herein, and unless stated otherwise, each of the following terms shall have the definition set forth below.

| | |
|---|---|
| A | Adenine; |
| C | Cytosine; |
| DNA | Deoxyribonucleic acid; |
| G | Guanine; |
| RNA | Ribonucleic acid; |
| T | Thymine; and |
| U | Uracil. |

"Electronic signature" of a nucleotide passing through a pore via application of an electronic field shall include, for example, the duration of the nucleotide's passage through the pore together with the observed amplitude of current during that passage. Electronic signatures can be visualized, for example, by a plot of current (e.g. pA) versus time. Electronic signature for a DNA is also envisioned and can be, for example, a plot of current (e.g. pA) versus time for the DNA to pass through the pore via application of an electric field.

"Nanopore" includes, for example, a structure comprising (a) a first and a second compartment separated by a physical barrier, which barrier has at least one pore with a diameter, for example, of from about 1 to 10 nm, and (b) a means for applying an electric field across the barrier so that a charged molecule such as DNA can pass from the first compartment through the pore to the second compartment. The nanopore ideally further comprises a means for measuring the electronic signature of a molecule passing through its barrier. The nanopore barrier may be synthetic or naturally occurring in part. Barriers can include, for example, lipid bilayers having therein α-hemolysin, oligomeric protein channels such as porins, and synthetic peptides and the like. Barriers can also include inorganic plates having one or more holes of a suitable size. Herein "nanopore", "nanopore barrier" and the "pore" in the nanopore barrier are sometimes used equivalently.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to A, G, C, T or U.

Embodiments of the Invention

This invention provides a method for determining the nucleotide sequence of a single-stranded DNA comprising the steps of:
(a) passing the single-stranded DNA through a pore of suitable diameter by applying an electric field to the DNA, wherein at least each A or each G residue and at least each C, each T or each U residue comprises a modifying group bound to its respective base so that each type of nucleotide in the DNA has an electronic signature which is distinguishable from the electronic signature of each other type of nucleotide in the DNA;
(b) for each nucleotide of the DNA which passes through the pore, determining an electronic signature for such nucleotide; and
(c) comparing each electronic signature determined in step (b) with electronic signatures corresponding to each of A, G, C and T modified as per the nucleotides in the single-stranded DNA, so as to determine the identity of each such nucleotide, thereby determining the nucleotide sequence of the single-stranded DNA.

In an embodiment of the instant method, the single-stranded DNA is obtained by (a) synthesizing double-stranded DNA using a single-stranded template, a DNA polymerase and nucleotides, wherein at least each A or each G residue and at least each C or each T residue comprises a modifying group bound to its respective base so that each type of nucleotide in the DNA has an electronic signature which is distinguishable from the electronic signature of each other type nucleotide in the DNA, and (b) removing from the resulting double-stranded DNA the single-stranded DNA containing modified nucleotides.

In another embodiment of the instant method, the single-stranded DNA is obtained by (a) synthesizing double-stranded DNA using a single-stranded template, a DNA polymerase and nucleotides, wherein at least each A, each G, each C, each U or each T residue comprises an azido group bound to its base, and at least each A, each G, each C, each U and each T comprises an amino group bound to its base, whereby the azido and amino groups do not reside on the same type of base, (b) removing from the resulting double-stranded DNA the single-stranded. DNA containing the azido and amino group-containing nucleotides and (c) reacting the resulting single-stranded DNA with a first modifying group which forms a bond with the azido group and a second modifying group which forms a bond with the amino group so as to obtain the single-stranded DNA.

This invention also provides a method for determining the nucleotide sequence of a single-stranded RNA comprising the steps of:
(a) passing the single-stranded RNA through a pore of suitable diameter by applying an electric field to the RNA, wherein at least each A or each G residue and at least each C or each U residue comprises a modifying group bound to its respective base so that each type of nucleotide in the RNA has an electronic signature which is distinguishable from the electronic signature of each other type of nucleotide in the RNA;

(b) for each nucleotide of the RNA which passes through the pore, determining an electronic signature for such nucleotide; and (c) comparing each electronic signature determined in step (b) with electronic signatures corresponding to each of A, G, C and U modified as per the nucleotides in the single-stranded RNA, so as to determine the identity of each such nucleotide, thereby determining the nucleotide sequence of the single-stranded RNA.

In an embodiment of the instant method, the single-stranded RNA is obtained by (a) synthesizing double-stranded RNA using a single-stranded template, an RNA polymerase and nucleotides, wherein at least each A, each G, each C or each U residue comprises an azido group bound to its base, and at least each A, each G, each C and each U comprises an amino group bound to its base, whereby the azido and amino groups do not reside on the same type of base, (b) removing from the resulting double-stranded RNA the single-stranded RNA containing the azido and amino group-containing nucleotides and (c) reacting the resulting single-stranded RNA with a first modifying group which forms a bond with the azido group and a second modifying group which forms a bond with the amino group so as to obtain the single-stranded RNA.

In another embodiment of the instant method, the single-stranded RNA is obtained by (a) synthesizing double-stranded RNA using a single-stranded template, an RNA polymerase and nucleotides, wherein at least each A or each G residue and at least each C or each U residue comprises a modifying group bound to its respective base so that each type of nucleotide in the RNA has an electronic signature which is distinguishable from the electronic signature of each other type nucleotide in the RNA, and (b) removing from the resulting double-stranded RNA the single-stranded RNA containing modified nucleotides.

In one embodiment of the instant methods, the pore has a diameter of from about 1 nm to about 5 nm. In a further embodiment of the instant methods, the pore has a diameter of from about 1 nm to about 3 nm. In embodiments of the instant methods, the pore has a diameter of about 1 nm, 2 nm, 3 nm, 4 nm or 5 nm. In further embodiments, the pore is, for example, about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 nm in diameter.

In one embodiment, a single pore is employed. In another embodiment, multiple pores are employed.

Nanopore devices are known in the art. See, for example, references [24] through [34]. Nanopores and methods employing them are disclosed in U.S. Pat. No. 7,005,264 B2 and U.S. Pat. No. 6,617,113 which are, hereby incorporated by reference in their entirety.

In one embodiment of the instant methods, each A and each T or each U residue comprises a modifying group; each A and each U residue comprises a modifying group; and/or each G and each C residue comprises a modifying group.

Moieties used to modify nucleotides can differ in size and/or charge, so long as each type of nucleotide in a nucleic acid whose sequence is being determined by the instant methods has an electronic signature which differs from each other type.

DNA polymerases which can be used in the instant invention include, for example *E. Coli* DNA polymerase I, Bacteriophage T4 DNA polymerase, Sequenase™, Taq DNA polymerase and 9° N polymerase (exo-) A485L/Y409V.RNA polymerases which can be used in the instant invention include, for example, Bacteriophage SP6, T7 and T3 RNA polymerases.

This invention also provides a nucleotide having an azido group covalently bound to its base. In one embodiment, the nucleotide is dUTP and the azido group is bound to the base at the 5-position. In one embodiment, the nucleotide is DATP and the azido group is bound to the base at the 8-position. In another embodiment, the nucleotide is dGTP and the azido group is bound to the base at the 8-position. The azido and amino groups can also be any other groups which permit binding of a unique moiety to each type of nucleotide.

This invention also provides a method for making a modified nucleotide comprising contacting the instant nucleotide with an alkyne-containing compound under conditions permitting reaction between the azido and the alkyne groups, thereby making the modified nucleotide.

This invention will be better understood by reference to the Experimental Details which follow, but those skilled in the art will readily appreciate that the specific experiments detailed are only illustrative of the invention as described more fully in the claims which follow thereafter.

Experimental Details

Figure 2:
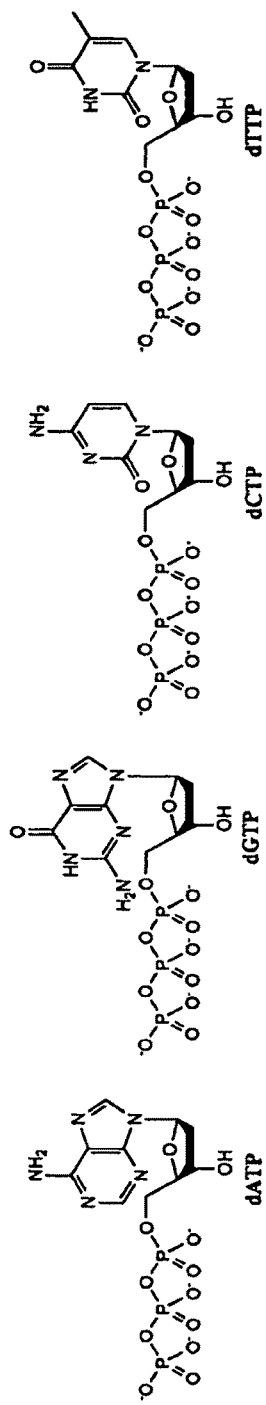
FIG. 2. Structures of nucleotides dATP, dGTP, dCTP and dTTP.

The structures of the four nucleotides are shown in FIG. 2. A and G are purines, while C and T are pyrimidines. The overall molecular sizes of A and G are very similar, while the sizes of C and T are similar. Thus, nanopore has been shown to be able to differentiate between purines and pyrimidines [1 and 14], but not to be able to distinguish between individual purinee, A and G, or between individual pyrimidines, C and T.

Disclosed here is the design of modified nucleotides to enhance discrimination of each nucleotide by modifying A and T. Since A and G are bulky purines similar in size, they will generate similar blocking current signatures (also called electronic signatures) in the nanopore. Likewise C and T, both pyrimidines, will generate similar signatures. The site selected for modification is on the 7-position of A and the 5-position of T nucleotide molecules. The 7-position of A and the 5-position of T have been shown to be chemically modified with bulky groups while not affecting basic DNA properties, such as forming the double-stranded DNA structure and being able to carry out polymerase reactions [2, 13 and 17]. These modifications will enlarge the discrimination of the bases by nanopore due to the increased size differences between the four nucleotides (A, G, C and T). In addition, the DNA translocation rate through the nanopore is expected to slow down due to the bulkiness of the modified nucleotides. Thus, achieving the accuracy and reliability required for the base-to-base sequencing is envisioned. The overall analytical parameters in the nanopore sequencing, such as concentration of the polynucleotide, magnitude of applied voltage, temperature and pH value of the solution, are optimized in order to get the most accurate and reliable results for the detection and analysis of the DNA chain.

Use of Synthetic DNA Carrying Bulky Groups for Detection by Nanopore

In order to investigate the effect of nucleotide bulkiness on electronic blockade signals generated by the nanopore, various polynucleotides are synthesized with different bulky groups attached to the base of the nucleotide by a DNA synthesizer. Initially, regular C's and G's are used to synthesize a series of polynucleotides (FIGS. 3a and 3b). In addition, a series of polynucleotides using modified A's (6-aminohexylamino attached to the 8-position of the base) and modified T's (BIOTIN attached to the 5-position of the base)

Figure 3:
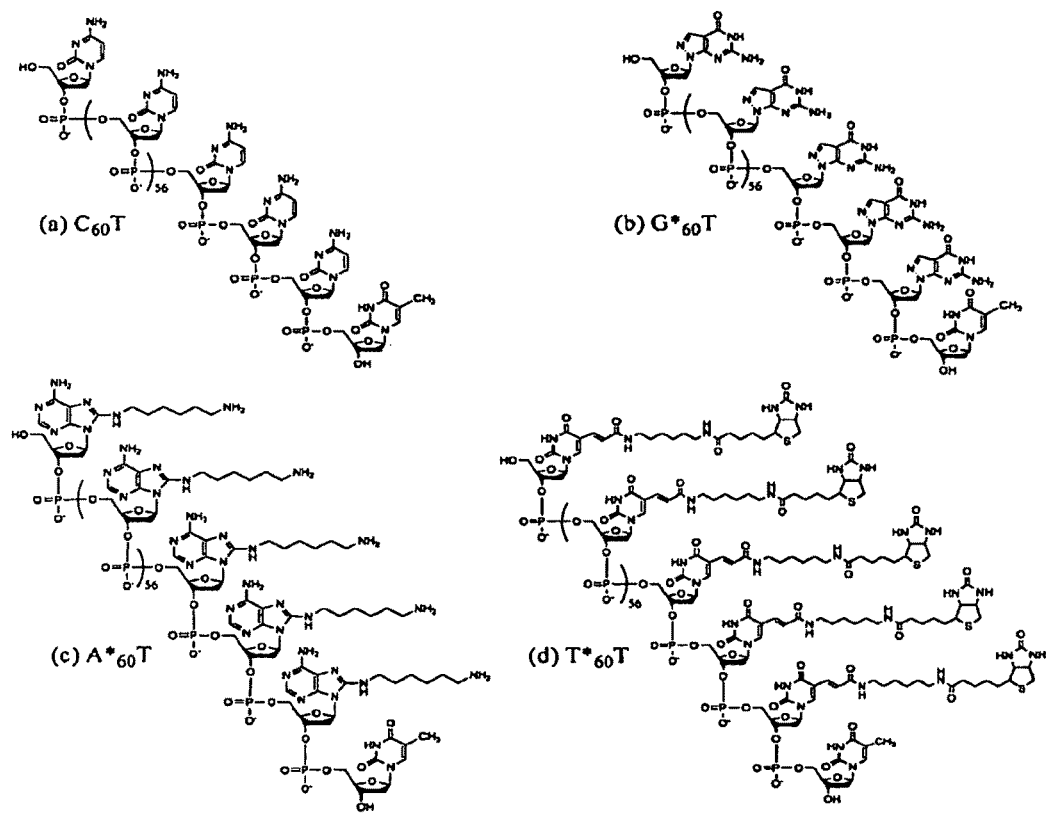
FIG. 3. Nucleotide bulkiness in ascending order: (a) 5'-$C_{60}$T-3', (b) 5'-$G^*_{60}$T-3', (c) 5'-$A^*_{60}$T-3', and (d) 5'-T*60T-3'.

(FIGS. 3c and 3d), which increase the bulkiness of the nucleotides, are synthesized. The order of the bulkiness of the nucleotides in FIG. 3 is as follows: T*>A*>G>C. These polynucleotides are then passed through the nanopore to identify the relationship between the bulky groups attached to the base and the difference in electronic blockade signal between the different bases.

Attachment of Bulky Groups to Nucleotides for Nanopore Detection (1) Design and Synthesis of Modified Nucleotides (dATP-NHCOR$_1$ and dUTP-NHCOR$_2$).

Figure 4:
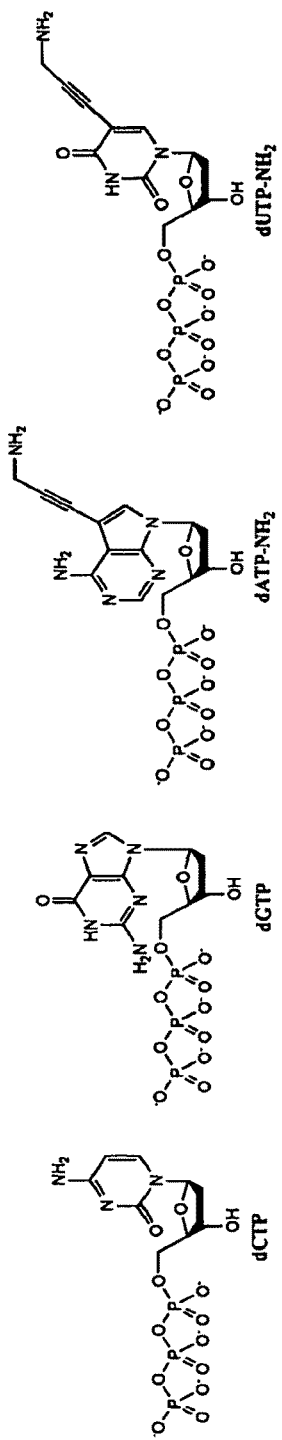
FIG. 4. Structures of dCTP and dGTP, and modified nucleotides (dATP-$NH_2$ and dUTP-$NH_2$).
Figure 5:
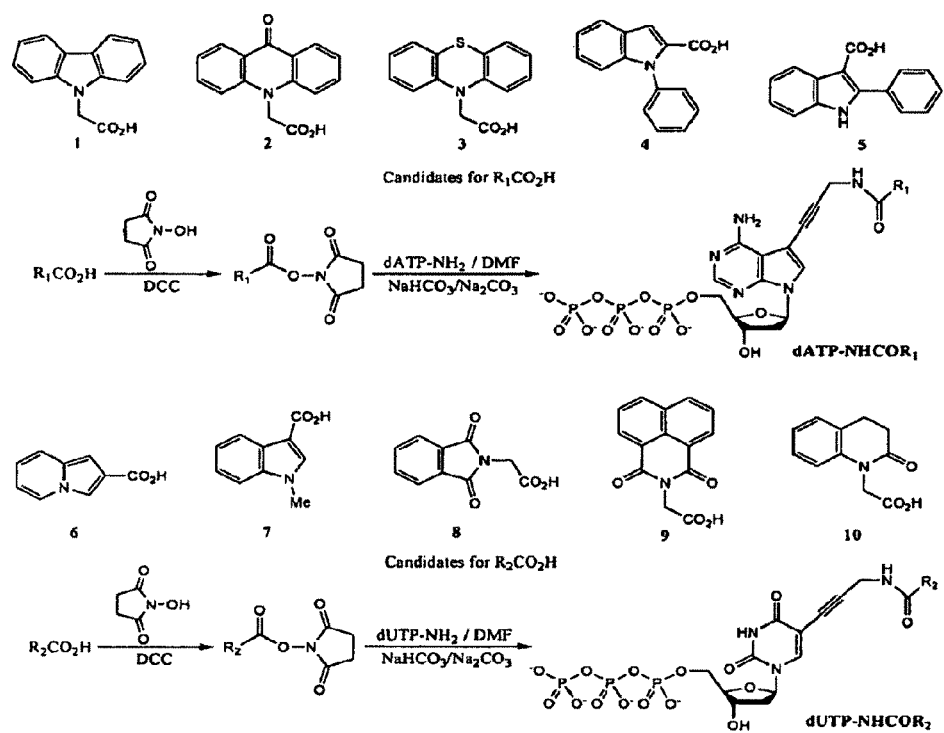
FIG. 5. Modification of dATP-$NH_2$ and dUTP-$NH_2$.

Synthesized dATP-NH$_2$ and dUTP-NH$_2$ are used as starting materials for further nucleotide modification while unmodified dCTP and dGTP are used directly (FIG. 4). The routes of nucleotide modification are shown in FIG. 5. The commercially available carboxylic acids 1~10 will be converted into the corresponding N-hydroxysuccinimidyl (NHS) esters conveniently using N-hydroxysuccinimide and DCC [20 and 22]. Then the nucleotides for modification (dATP-NH$_2$ and dUTP-NH$_2$) will be connected with the modification groups R$_1$ and R$_2$ respectively in DMF and NaHCO$_3$/Na$_2$CO$_3$ buffer solution [13 and 17]. After modification, the order of nucleotide bulkiness will be: A*>U*>G>C, as purines (A and G) are larger than pyrimidines (C and U) and in general the modification group R$_1$ is larger than R$_2$.

(2) DNA-Extension Reaction Using Modified Nucleotides (dATP-NHCOR$_1$ and dUTP-NHCOR$_2$).

Figure 6:
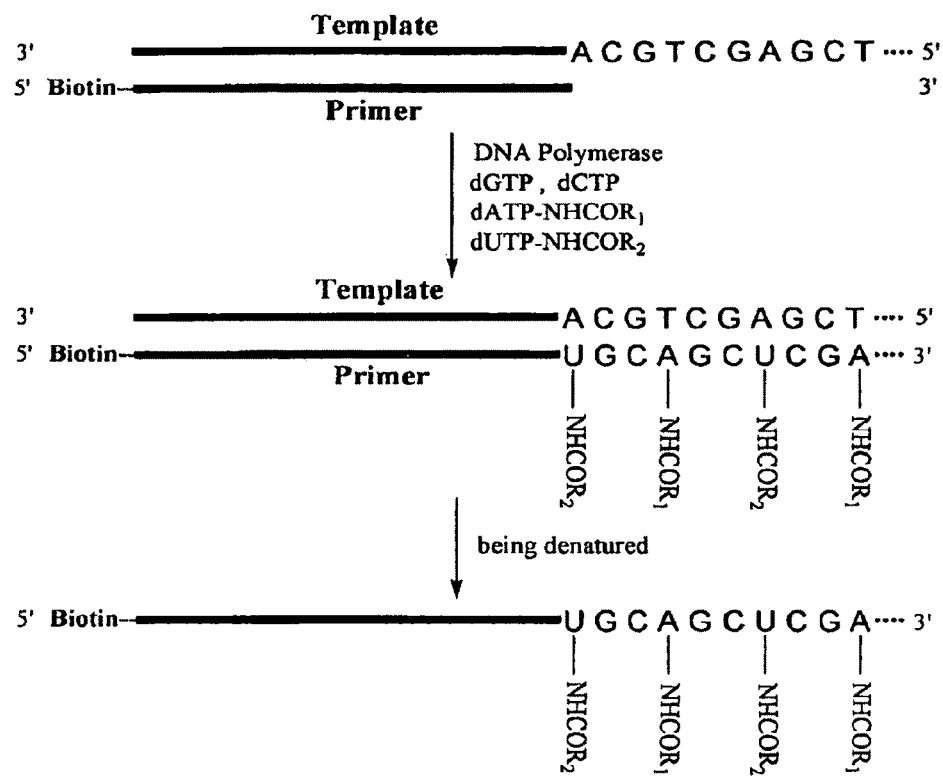
FIG. 6. DNA-extension reaction using modified nucleotides (dATP-NHCOR$_1$ and dUTP-NHCOR$_2$) to generate a modified single-stranded DNA chain. (SEQ ID NOs. 1 and 2 for template and primer, respectively).

The modified DATP and dUTP, and the unmodified dCTP and dGTP, are then be used in a polymerase reaction to generate single-stranded DNA. As shown in FIG. 6, after the polymerase reaction, the single-stranded DNA chain is obtained after being denatured from the template chain, which is composed of the modified DATP and dUTP as well as unmodified dCTP and dGTP. The 5'-end of the primer chain is modified on the base by a biotin moiety to isolate only DNA product that has incorporated the modified nucleotides. These modified single-stranded chains are then used in the nanopore by single-channel recording techniques for sequencing sensitivity and accuracy evaluation.

DNA-Sequencing Study by Nanopore

Figure 7:
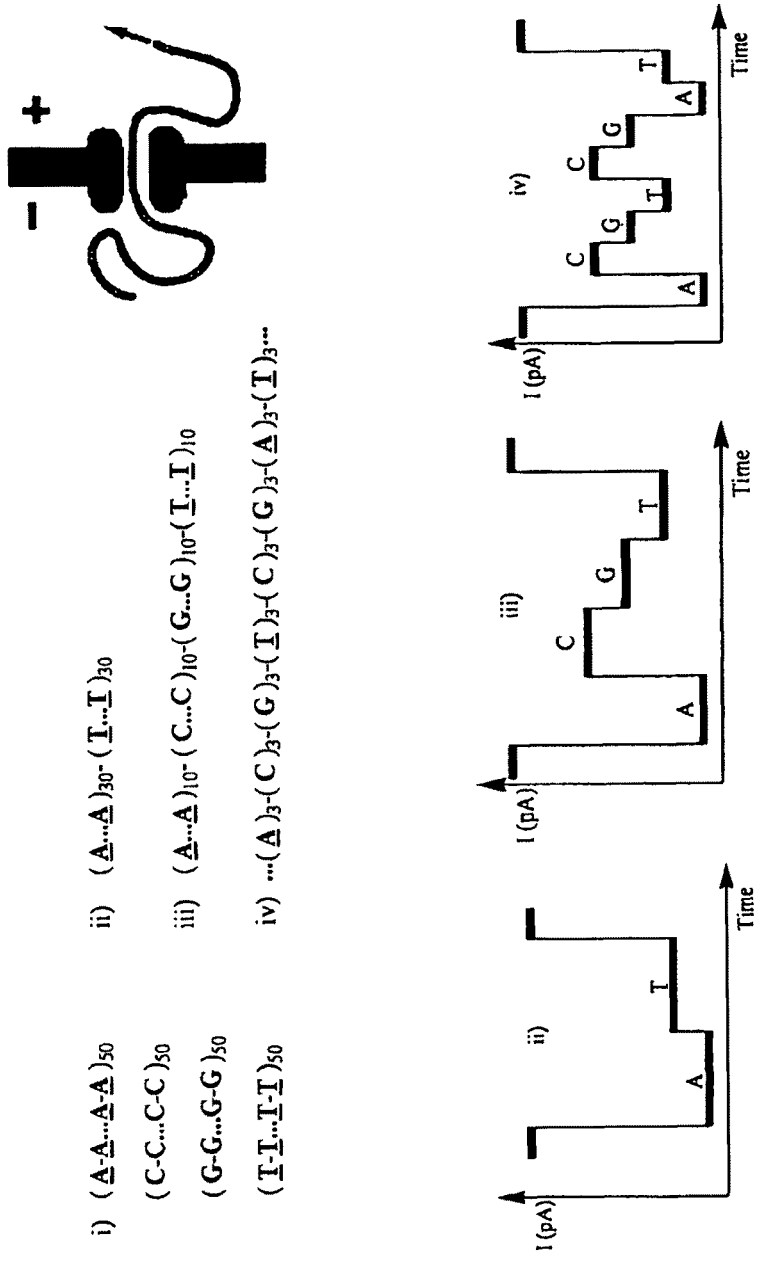
FIG. 7. Steps of verifying sequencing capacity via nanopore using various DNA sequences. (SEQ ID NOs. 3-6 for part (i), top to bottom, respectively; SEQ ID NO:7 for part (ii); SEQ ID NO:8 for part (iii); and SEQ ID NO:9 for part (iv)).

To validate nanopore's ability to distinguish the four different nucleotides in DNA, a series of tests are conducted as shown in FIG. 7. First, a polynucleotide stretch composed of only 50 identical nucleotides (i) is prepared by polymerase reaction as described above. Each DNA sequence is expected to generate different electronic blockade signatures due to the larger size difference of the nucleotides. The modification effects of R$_1$ and R$_2$ for A and T can be compared for preliminary optimization. Next, a polynucleotide stretch composed of 30 modified Ala and 30 modified T's (ii) is prepared and then tested in nanopore to demonstrate that the electronic blockade signatures differ in magnitude between A and T and are easily distinguishable.

Based on the signatures generated, the candidates for R$_1$ and R$_2$ groups are selected to achieve the best discrimination in signal. Third, a shorter polynucleotide stretch composed of 10 A's, 10 C's, 10 G's and 10 T's (iii) are prepared and tested in nanopore for further confirmation on the electronic blockade signatures (also called electronic signatures). Finally, a polynucleotide stretch composed of three consecutive A-C-G-T sequence (iv) is prepared and tested in nanopore. The detailed sequencing conditions can be optimized according to known methods. Based on these results, random DNA chain with modified A and T and unmodified C and G is evaluated for accurate detection and discrimination by the nanopore. These procedures allow characterization of the signals from each of the nucleotides and the transitions between nucleotides of different identities. The magnitude and duration of the blockade signatures on the event diagram are then analyzed and compared with known diagrams for validation. The schematic of the predicted blockade signals from DNA molecules (ii), (iii) and (iv) are shown in FIG. 7. Thus, with these rational chemical designs and modifications of the building blocks of DNA, this invention envisions using nanopore to decipher DNA sequences at the single molecule level with single base resolution.

Attach Small Hooks to the Nucleotides for Synthesis of DNA in Polymerase Reaction for Nanopore Detection If a DNA polymerase is not able to synthesize a long strand of DNA due to the bulkiness of the functional groups introduced, an alternative strategy is to introduce small 'hooks' to the nucleotides, then perform polymerase reaction to produce DNA products with hook-labeled nucleotides incorporated in them.

The DNA products are then linked with the large functional groups through the hook for distinct detection by nanopore.

(1) Design and Synthesis of Hook-Labeled Nucleotide duTP-N$_3$.

Figure 8:
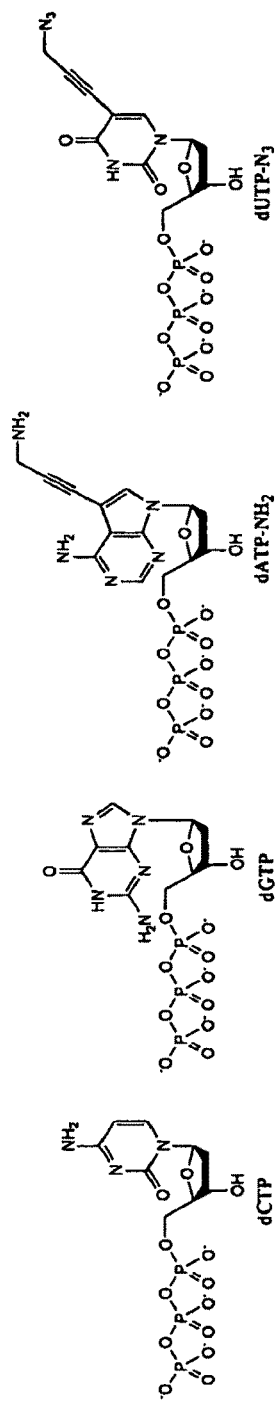
FIG. 8. Structures of unmodified nucleotides (dCTP and dGTP) and hook-labeled nucleotides (dATP-NH$_2$ and dUTP-N$_3$). The amino and the azido groups function as hooks to conjugate with bulky groups after the nucleotides are incorporated into the DNA strand.
Figure 9:
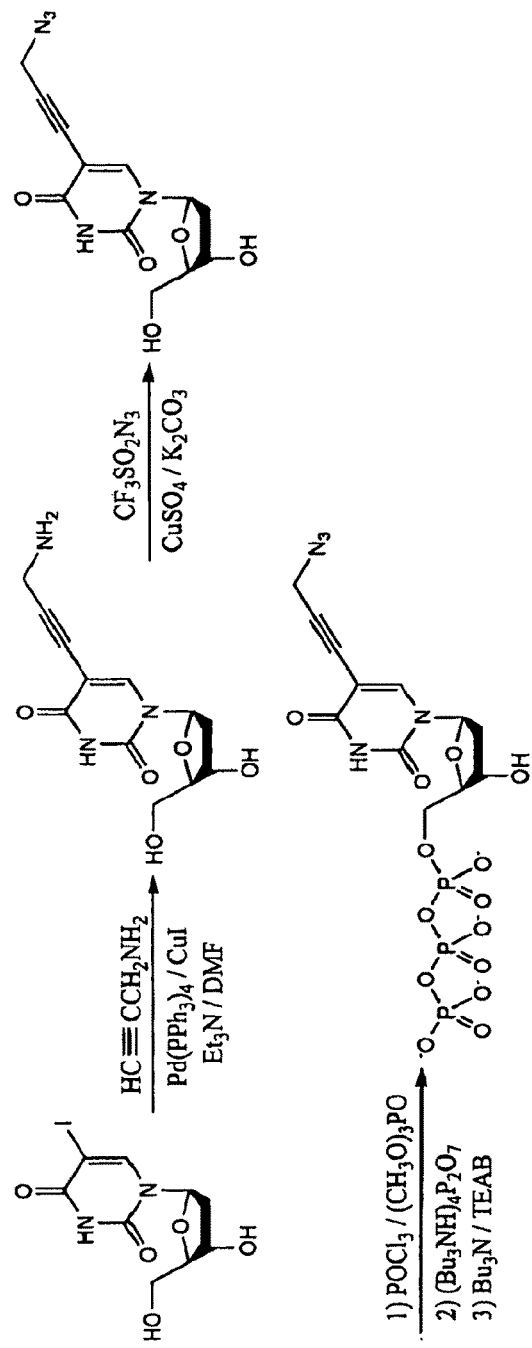
FIG. 9. Synthesis of dUTP-N$_3$.

The available dCTP, dGTP and dATP-NH$_2$ are used as starting materials directly (FIG. 8), while dUTP-N$_3$ is synthesized from 5-iodo-2'-deoxyuridine as shown in FIG. 9. 5-Iodo-2'-deoxyuridine is first coupled with propargylamine in the presence of palladium(0) and copper(I) catalysts. Then the amino group is converted into azido group by the diazo transfer method [11]. Finally triphosphate is introduced to the 5'-hydroxy group of the nucleoside to yield dUTP-N$_3$ [6].

(2) DNA-Extension Reaction Using Hook-Labeled Nucleotides (dATP-NH$_2$ and dUTP-N$_3$).

Figure 10:
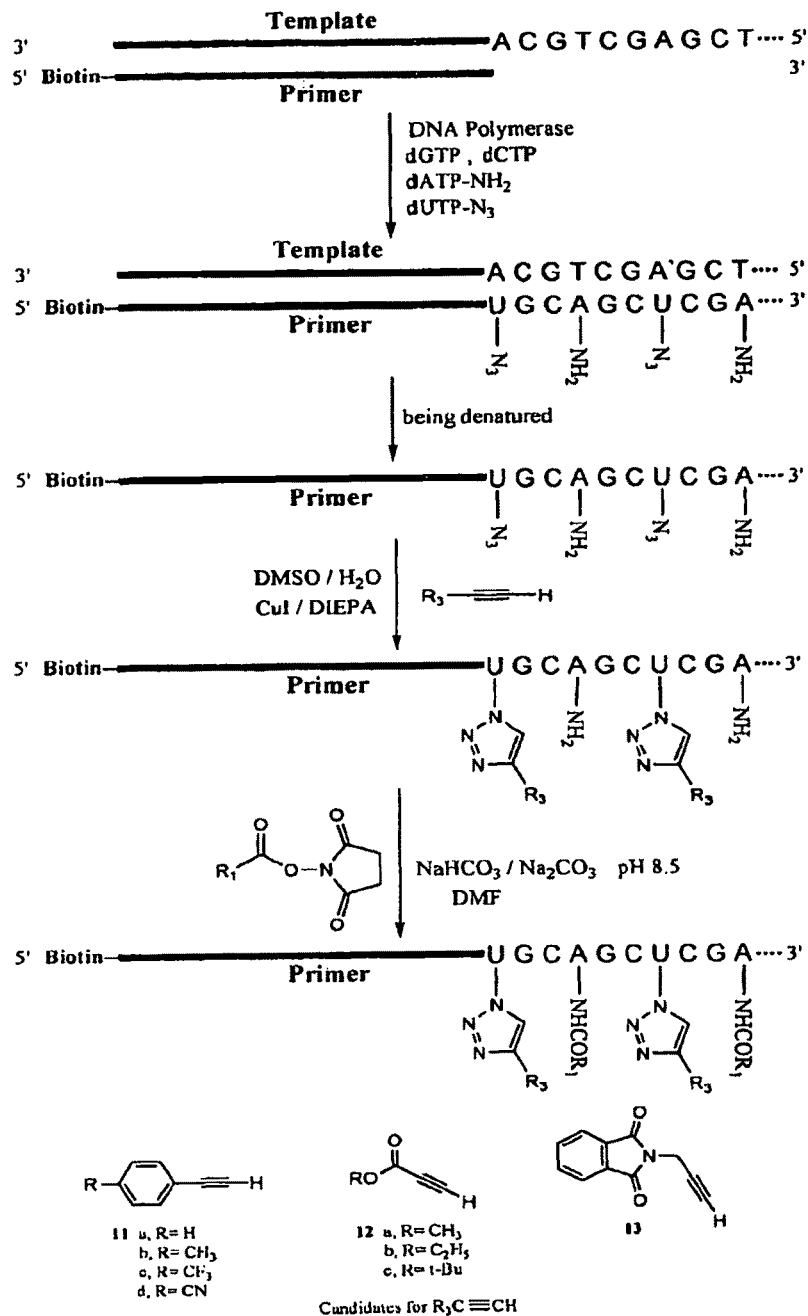
FIG. 10. DNA-extension reaction using hook-labeled nucleotides (dATP-NH$_2$ and dUTP-N$_3$) to generate a modified single-stranded DNA chain, which will then react with large functional groups (R1 and R3) selectively for distinct detection by nanopore. (SEQ ID NOs. 1 and 2 for template and primer, respectively)

The dATP-NH$_2$ and dUTP-N$_3$, and the unmodified dCTP and dGTP, are used in polymerase reaction on the single-stranded nucleic acid template to obtain hook-labeled DNA products. Due to the small sizes of the azido and amino groups, these nucleotides are expected to be good substrates of commonly used DNA polymerases. After isolation of the single stranded DNA carrying the hook, the azido groups on these modified DNA chains will be further modified by Huisgen 1,3-dipolar cycloaddition with terminal alkynes (R$_3$C≡CH) in the presence of copper(I) catalyst (FIG. 10) [18 and 19]. The amino groups on the "A" nucleotides of these modified DNA chains are connected with the modification groups R$_1$ in DMF and NaHCO$_3$/Na$_2$CO$_3$ buffer solution [13 and 17]. After modification, the order of nucleotides bulkiness on the chain will be: A*>U*>G>C since in general the modification group R$_1$ is larger than R$_3$.

Nanopore Contruction and Detection of DNA

Based on information in the art, nanopores are constructed with different configurations and modifications for characterizing DNA containing nucleotides of different sizes.

Synthetic nanopores are described in references [24] through [28] which are hereby incorporated by reference in their entirety. The mechanics and kinetics of DNA passage through the pores are described in references [29] and [30], respectively.

Natural nanopores are described in references [31] through [34] which are hereby incorporated by reference in their entirety.

REFERENCES

1. Akeson, M., Branton, D., Kasianowicz, J. J., Brandin, E. and Deamer, D. W. Microsecond time-scale discrimination between polycytidylic acid and polyadenylic acid segments within single RNA molecules. *Biophys. J.*, 1999, 77, 3227-3233.

2. Bai, X., Kim, S., Li, Z., Turro, N. J. and Ju, J. Design and synthesis of a photocleavable biotinylated nucleotide for DNA analysis by mass spectrometry. *Nucleic Acids Research* 2004, 32(2), 535-541.
3. Bezrukov, S. M., and Kasianowicz, J. J. Neutral polymers in the nanopores of alamethicin and alpha-hemolysin. *Biologicheskie Membrany* 2001, 18, 453-457.
4. Chandler, E. L., Smith, A. L., Burden, L. M., Kasianowicz and Burden, D. L. Membrane Surface Dynamics of DNA-Threaded Nanopores Revealed by Simultaneous Single-Molecule Optical and Ensemble Electrical Recording. *Lanzgmuir* 2004, 20, 898-905.
5. Deamer, D. W. and Branton, D. Characterization of nucleic acids by nanopore analysis. *Acc. Chem. Res.* 2002, 35(10), 817-825.
6. Lee S. E., Sidorov A., Gourlain T., Mignet N., Thorpe S. J., Brazier J. A., Dickman M. J., Hornby D. P., Grasby, J. A. and Williams, D. M. Enhancing the catalytic repertoire of nucleic acids: a systematic study of linker length and rigidity. *Nucleic Acids Research* 2001, 29(7), 1565-1573.
7. Henrickson, S. E., Misakian, M., Robertson, B. and Kasianowicz, J. J. Driven asymmetric DNA transport in a nanometer-scale pore. *Physical Review Letters* 2000, 85, 3057-3060.
8. Kasianowicz, J. J., Brandin, B., Branton, D. and Deamer, D. W. Characterization of individual polynucleotide molecules using a membrane channel. *Proc. Natl. Acad. Sci. USA* 1996, 93, 13770-13773.
9. Kasianowicz, J. J. Nanometer-scale pores: potential applications for DNA characterization and analyte detection. *Disease Markers* 2003, 18, 185-191.
10. Kasianowicz, J. J. Nanopore. Flossing with DNA. *Nature Materials* 2004, 3, 355-356.
11. Lundquist, J. T. and Pelletier, J. C. A New Tri-Orthogonal Strategy for Peptide Cyclization. *Org. Lett.* 2002, 4(19), 3219-3221.
12. Li, L., Stein, D., McMullan, C., Branton, D., Aziz, M. J. and Golovchenko, J. A. Ion-beam sculpting at nanometer length scales. *Nature* 2001, 412, 166-169.
13. Li, Z., Bai, X., Ruparel, H., Kim, S., Turro, N. J. and Ju, J. A photocleavable fluorescent nucleotide for DNA sequencing and analysis. *Proc. Natl. Acad. Sci. USA* 2003, 100, 414-419.
14. Meller, A., Nivon, L., Brandin, E., Golovchenko, J. and Branton, D. Rapid nanopore discrimination between single polynucleotide molecules. *Proc. Natl. Acad. Sci. USA* 2000, 97, 1079-1084.
15. Perkins, T. T., Quake, S. R., Smith, D. E. and Chu, S. Relaxation of a single DNA molecule observed by optical microscopy. *Science* 1994, 264, 822-826.
16. Rief, M., Clausen-Schaumann, H. and Gaub, H. E. Sequence-dependent mechanics of single DNA molecules. *Nat. Struct. Biol.* 1999, 6, 346-349.
17. Rosenblum, B. B., Lee, L. G., Spurgeon, S. L., Khan, S. H., Menchen, S. M., Heiner, C. R. and Chen, S. M. New dye-labeled terminators for improved DNA sequencing patterns. *Nucleic Acids Research* 1997, 25(22), 4500-4504.
18. Rostovtsev, V. V., Green, L. G., Fokin, V. V. and Sharpless, K. B. A stepwise huisgen cycloaddition process: copper(I)-catalyzed regioselective "ligation" of azides and terminal alkynes. *Angew. Chem. Int. Ed.* 2002, 41(14), 2596-2599.
19. Seo, T. S., Bai, X., Ruparel, H., Li, Z., Turro, N. J. and Ju, J. Photocleavable fluorescent nucleotides for DNA sequencing on a chip constructed by site-specific coupling chemistry. *Proc. Natl. Acad. Sci. USA* 2004, 101, 5488-5493.
20. Singh, S. B. and Tomassini, J. E. Synthesis of natural flutimide and analogues fully substituted pyrazine-2,6-diones, endonuclease inhibitors of influenza virus. *J. Org. Chem.* 2001, 66(16), 5504-5516.
21. Smith, S. B., Cui, Y. and Bustamante, C. Overstretching B-DNA: the elastic response of individual double-stranded and single-stranded DNA molecules. *Science* 1996, 271, 795-799.
22. Streater, M., Taylor, P. D., Hider, R. C., and Porter, J. Novel 3-hydroxy-2(1H)-pyridinones. Synthesis, iron(III)-chelating properties, and biological activity. *J. Medicinal Chem.* 1990, 33(6), 1749-1755.
23. Vercoutere, W., Winters-Hilt, S., Olsen, H., Deamer, D., Haussler, D. and Akeson, M. Rapid discrimination among individual DNA hairpin molecules at single-nucleotide resolution using an ion channel. *Nat. Biotech* 2001, 19, 248-252.
24. Heng, J. B. et al., The Electromechanics of DNA in a synthetic Nanopore. *Biophysical Journal* 2006, 90, 1098-1106.
25. Fologea, D. et al., Detecting Single Stranded DNA with a Solid State Nanopore. *Nano Letters* 2005 5(10), 1905-1909.
26. Heng, J. B. et al., Stretching DNA Using the Electric Field in a Synthetic Nanopore. *Nano Letters* 2005 5(10), 1883-1888.
27. Fologea, D. et al., Slowing DNA Translocation in a Solid State Nanopore. *Nano Letters* 2005 5(9), 1734-1737.
28. Bokhari, S. H. and Sauer, J. R., A Parallel Graph Decomposition Algorithm for DNA Sequencing with Nanopores. *Bioinformatics* 2005 21(7), 889-896.
29. Mathe, J. et al., Nanopore Unzipping of Individual Hairpin Molecules. *Biophysical Journal* 2004 87, 3205-3212.
30. Aksimentiev, A. et al., Microscopic Kinetics of DNA Translocation through Synthetic Nanopores. *Biophysical Journal* 2004 87, 2086-2097.
31. Wang, H. et al., DNA heterogeneity and Phosphorylation unveiled by Single-Molecule Electrophoresis. *PNAS* 2004 101(37), 13472-13477.
32. Sauer-Budge, A. F. et al., Unzipping Kinetics of Doubel Stranded DNA in a Nanopore. *Physical Review Letters* 2003 90(23), 238101-1-238101-4.
33. Vercoutere, W. A. et al., Discrimination Among Individual Watson-Crick Base Pairs at the Terminin of Single DNA Hairpin Molecules. *Nucleic Acids Research* 2003 31(4), 1311-1318.
34. Meller, A. et al., Single Molecule Measurements of DNA Transport Through a Nanopore. *Electrophoresis* 2002 23, 2583-2591.

What is claimed is:

1. A method for determining the nucleotide sequence of a single-stranded DNA comprising the steps of:
   (a) synthesizing a precursor of the single-stranded DNA as part of a double-stranded DNA using a single-stranded DNA template, a primer, a DNA polymerase, and all four nucleotides present in DNA, wherein each A or each G residue, but not both, comprise a first label bound to its respective base, and each C or each T residue, but not both, comprise a second label bound to its respective base;
   (b) denaturing the double-stranded DNA obtained in (a);
   (c) isolating the single-stranded DNA to be sequenced comprising the nucleotides containing the first label and the second label from the denatured double-stranded DNA;
   (d) reacting the single-stranded DNA isolated in (c) with first modifying groups which form bonds with the first labels and second modifying groups which form bonds with the second labels, so as to obtain the single-stranded DNA to be sequenced wherein each labeled nucleotide is conjugated to a modifying group;
   (e) passing the single-stranded DNA to be sequenced through a pore of suitable diameter by applying and electric field to the DNA:
   (f) determining an electronic signature for each nucleotide of the single-stranded DNA which passes through the pore; and
   (g) comparing each electronic signature determined in (f) with electronic signatures corresponding to each of A, G, C, and T or corresponding to the bases conjugated to the modifying group, so as to determine the identity of each such nucleotide,
   thereby determining the nucleotide sequence of the single-stranded DNA.

2. The method of claim 1, wherein the pore has a diameter of from about 1 nm to about 5 nm.

3. The method of claim 1, wherein the pore has a diameter of from about 1 nm to about 3 nm.

4. The method of claim 1, wherein the pore has a diameter of about 1 nm, 2 nm, 3 nm, 4 nm or 5 nm.

5. The method of claim 1, wherein each A and each T nucleotide comprises a modifying group bound to its labeled base.

6. The method of claim 1, wherein each G and each C nucleotide comprises a modifying group bound to its labeled base.

7. The method of claim 1, wherein each A and each C residue or each G and each T residue comprises a modifying group bound to its respective base.

8. The method of claim 1, wherein 5'-end of the primer comprises a biotin moiety.

9. The method of claim 1, wherein the first label is an amino group and the second label is an azido group.

10. The method of claim 1, wherein the first label is an azido group and the second label is an amino group.

11. A method for determining the nucleotide sequence of a single-stranded DNA comprising the steps of:
   (a) passing the single-stranded DNA through a nanopore of a suitable diameter by applying an electric field, wherein each A or each G residue, but not both, comprises a modifying group bound to a label added to its respective base, and each C or each T residue, but not both, comprises a modifying group bound to a label added to its respective base, and each type of nucleotide in the single-stranded DNA has a characteristic electronic signature which is distinguishable from the electronic signature of all other types of nucleotides in the single-stranded DNA;
   (b) determining the electronic signature for each nucleotide within the single-stranded DNA which passes through the nanopore
   (c) comparing each electronic signature determined in step (b) with the electronic signature characteristic of each type of nucleotide so as to determine the identity of each such nucleotide that passes through the nanopore;
   thereby determining the nucleotide sequence of the single-stranded DNA.

12. The method of claim 11, wherein the nanopore has a diameter of from about 1 nm to about 5 nm.

13. The method of claim 11, wherein the single-stranded DNA whose sequence is to be determined is obtained by:
   (a) synthesizing the single-stranded DNA as part of a double-stranded DNA using a single-stranded DNA template, a primer, a DNA polymerase, and nucleotides, wherein each A or each G residue, but not both, comprises a modifying group bound to a label added to its respective, and each C or each T residue, but not both, comprises a modifying group bound to a label added to its respective base, wherein all of the A or G nucleotides, and all of the C or the T nucleotides within the single-stranded DNA comprise an identical modifying group bound to the label added to their respective bases and each type of nucleotide has a characteristic electronic signature which is distinguishable from the electronic signature of each other type of nucleotide in the DNA;

(b) denaturing the double-stranded DNA obtained in step (a); and (c) isolating the single-stranded DNA to be sequenced comprising modified nucleotides from the denatured double-stranded DNA.

14. The method of claim 11, wherein the single-stranded DNA whose sequence is to be determined is obtained by:

(a) synthesizing a precursor of the single-stranded DNA as part of a double-stranded DNA using a single-stranded DNA template, a primer, a DNA polymerase, and all four nucleotides present in DNA, wherein each A or each G residue, but not both, comprise a first label bound to its respective base, and each C or each T residue, but not both, comprise a second label bound to its respective base;

(b) denaturing the double-stranded DNA obtained in (a);

(c) isolating the single-stranded DNA to be sequenced comprising the first label and the second label-containing nucleotides from the denatured double-stranded DNA; and (d) reacting the single-stranded DNA isolated in (c) with first modifying groups which form bonds with the first labels and second modifying groups which form bonds with the second labels, so as to obtain the single-stranded DNA to be sequenced.

15. The method of claim 14, wherein the first label is an amino group and the second label is an azido group.

16. The method of claim 14, wherein the first label is an azido group and the second label is an amino group.

17. The method of claim 11, wherein each A nucleotide of said single stranded DNA comprises a modifying group bound to its labeled base.

18. The method of claim 11, wherein each T nucleotide of said single stranded DNA comprises a modifying group bound to its labeled base.

19. The method of claim 11, wherein A, G, C, and T nucleotides of said single-stranded DNA have an order of bulkiness that is T>A>G>C.

* * * * *